US006461385B1

(12) United States Patent
Gayer et al.

(10) Patent No.: US 6,461,385 B1
(45) Date of Patent: Oct. 8, 2002

(54) METHOD AND APPARATUS FOR AUGMENTING OSTEOINTEGRATION OF PROSTHETIC IMPLANT DEVICES

(75) Inventors: Gregory G. Gayer, Burlingame; Christopher J. Comfort, Sunnyvale, both of CA (US)

(73) Assignee: Comfort Biomedical Inc., Sunnyvale, CA (US)

( * ) Notice: Subject to any disclaimer, the term of this patent is extended or adjusted under 35 U.S.C. 154(b) by 0 days.

(21) Appl. No.: 09/651,826

(22) Filed: Aug. 30, 2000

Related U.S. Application Data

(62) Division of application No. 09/231,907, filed on Jan. 14, 1999, now Pat. No. 6,214,049, application No. 08/993,945, filed on Dec. 18, 1997, now abandoned, which is a division of application No. 09/236,164, filed on Jan. 22, 1999, now Pat. No. 6,143,036, and a division of application No. 09/236,167, filed on Jan. 22, 1999, now Pat. No. 6,077,076.

(51) Int. Cl.[7] .................................................. A61F 2/28
(52) U.S. Cl. ............................... 623/23.51; 623/23.54; 623/23.59; 623/23.6; 623/23.75; 623/23.76
(58) Field of Search ..................... 623/11.11, 16.11, 623/23.5, 23.51, 23.52, 23.53, 23.54, 23.55, 23.57, 23.74, 23.75, 23.76, 23.58, 23.59, 23.6, 23.61; 606/76

(56) References Cited

U.S. PATENT DOCUMENTS

| | | |
|---|---|---|
| 3,894,297 A | 7/1975 | Mettelmeier et al. |
| 3,905,777 A | 9/1975 | Lacroix |
| 3,906,550 A | 9/1975 | Rostoker et al. |
| 4,064,567 A | 12/1977 | Burstein et al. |
| 4,199,824 A | 4/1980 | Niederer |
| 4,261,063 A | 4/1981 | Blanquaert |
| 4,309,488 A | 1/1982 | Heide et al. |
| 4,394,370 A | 7/1983 | Jefferies |

(List continued on next page.)

OTHER PUBLICATIONS

Brian J. Cole, et al.: "Use of Bone Morphogenetic Protein 2 on Ectopic Porous Coated Implants in the Rat"; Clinical Orthopedics and Related Research; 1997 Lippincott–Raven Publishers; pp. 219–228.

Kevin A. Thomas; "Hydroxyapatite Coatings"; Mar. 1994, Orthopedics; vol. 17 No. 3; pp. 267–278.

David J. Baylink, et al.; "Growth Factors to stimulate Bone Formation"; 1993, Journal of Bone and Mineral Research vol. 8 No. 3; pp. S565–S572.

Stephen D. Cook, et al.; Hydroxyapatite–Coated Titanium for Orthopedic Implant Applications; Clinical Orthopedics and Related Research; Jul. 1998, No. 232; pp. 225–243.

R.J.B. Sakkers, et al.,; "Assessment of Bioactivity for Orthopedic Coatings in a Gap–Healing Model"; 1997 John Wiley & Sons, Inc.,; pp. 265–273.

*Primary Examiner*—Eduardo C. Robert
(74) *Attorney, Agent, or Firm*—Burgess & Bereznak, LLP

(57) ABSTRACT

Bone augmentation in a mammalian body to enhance the mechanical strength of a prosthesis is provided by reinforcement of bone in the region surrounding the implant device. A number of fibrillar wires are formed on the prosthetic implant device. Formation of the fibrillar wires comprises gauging the implant device so that the fibrillar wires are formed by peeling them from the implant device. Alternatively, formation of the fibrillar wires may comprise forming a mesh of fibrillar wires having a woolly structure, forming the mesh around the prosthetic implant device, and attaching a number of the fibrillar wires to the prosthetic implant device. A coating is formed on the fibrillar wires and an associated prosthetic implant device. The coating comprises bone morphogenetic proteins along with osteoinductive factors and osteoconductive factors that function as nutrients, anti-microbial and anti-inflammatory agents, and blood-clotting factors. The polymer is a polymer matrix component comprising lactic acid, glycolic acid, and copolymers of lactic acid and glycolic acid. The osteoinductive coating combined with the fibrillar wool or prongs should allow for optimal osteointegration and physiologic load distribution of a implant device resulting in prosthetic success when placed in the human body.

7 Claims, 7 Drawing Sheets

U.S. PATENT DOCUMENTS

| | | |
|---|---|---|
| 4,430,761 A | 2/1984 | Niederer et al. |
| 4,472,840 A | 9/1984 | Jefferies |
| 4,479,271 A | 10/1984 | Bolesky et al. |
| 4,483,678 A | 11/1984 | Nishio et al. |
| 4,526,909 A | 7/1985 | Urist |
| 4,530,116 A | 7/1985 | Frey |
| 4,535,487 A | 8/1985 | Esper et al. |
| 4,536,894 A | 8/1985 | Galante et al. |
| 4,549,319 A | 10/1985 | Meyer |
| 4,563,489 A | 1/1986 | Urist |
| 4,570,271 A | 2/1986 | Sump |
| 4,589,883 A | 5/1986 | Kenna |
| 4,608,053 A | 8/1986 | Keller |
| 4,636,219 A | 1/1987 | Pratt et al. |
| 4,660,755 A | 4/1987 | Farling et al. |
| 4,693,721 A | 9/1987 | Ducheyne |
| 4,795,472 A | 1/1989 | Crowninshield et al. |
| 4,829,152 A | 5/1989 | Rostoker et al. |
| 4,846,837 A | 7/1989 | Kurze |
| 4,923,513 A | 5/1990 | Ducheyne et al. |
| 4,960,649 A | 10/1990 | Shimamune et al. |
| 5,013,649 A | 5/1991 | Wang et al. |
| 5,018,285 A | 5/1991 | Zolman et al. |
| 5,030,233 A | 7/1991 | Ducheyne |
| 5,211,664 A | 5/1993 | Tepic et al. |
| 5,236,456 A | 8/1993 | O'Leary et al. |
| 5,344,457 A | 9/1994 | Pilliar et al. |
| 5,344,654 A | 9/1994 | Rueger et al. |
| 5,360,446 A | 11/1994 | Kennedy |
| 5,366,508 A | 11/1994 | Brekke |
| 5,373,621 A | 12/1994 | Ducheyne et al. |
| 5,458,653 A | 10/1995 | Davidson |
| 5,466,259 A | 11/1995 | Durette |
| 5,597,897 A | 1/1997 | Ron et al. |
| 5,606,019 A | 2/1997 | Cappello |
| 5,609,633 A | 3/1997 | Kokubo |
| 5,609,635 A | 3/1997 | Michelson |
| 5,629,009 A | 5/1997 | Laurencin et al. |
| 5,635,373 A | 6/1997 | Wozney et al. |
| 5,639,237 A | 6/1997 | Fontenot |
| 5,645,591 A | 7/1997 | Kuberasampath et al. |
| 5,652,118 A | 7/1997 | Ozkaynak et al. |
| 5,658,333 A | 8/1997 | Kelman et al. |
| 5,683,459 A | 11/1997 | Brekke |
| 5,702,446 A | 12/1997 | Schenck et al. |
| 5,707,962 A | 1/1998 | Chen et al. |
| 5,714,589 A | 2/1998 | Oppermann et al. |
| 5,733,564 A | 3/1998 | Lehtinen |
| 5,904,717 A | 5/1999 | Brekke et al. |
| 5,916,585 A * | 6/1999 | Cook et al. .............. 424/426 |
| 6,077,989 A * | 6/2000 | Kandel et al. .............. 623/16 |
| 6,143,036 A * | 11/2000 | Comfort .............. 623/23.54 |

\* cited by examiner

METHOD AND APPARATUS FOR AUGMENTING OSTEOINTEGRATION OF PROSTHETIC IMPLANT DEVICES

The present application is a divisional application of application No. 09/231,907, filed Jan. 14, 1999, entitled Method and Apparatus For Augmenting Osteointegration of Prosthetic Implant Devices, now Pat. No. 6,214,049, and is related to application No. 08/993,945, filed Dec. 18, 1997, entitled Bone Augmentation For Prosthetic Implants And The Like, now abandoned, which is the parent application of divisional application No. 09/236,164, filed Jan. 22, 1999, entitled Bone Augmentation For Prosthetic Implants And The Like, now U.S. Pat. No. 6,143,036, and divisional application No. 09/236,167, filed Jan. 22, 1999, entitled Bone Augmentation for Prosthetic Implants And The Like, now U.S. Pat. No. 6,077,076, all of which are assigned to the same assignee of the present application.

FIELD OF THE INVENTION

The present invention relates generally to the skeletal tissue regeneration field and, specifically, to devices and methods for inducing bone growth in skeletal areas supporting a prosthetic implant or in need of structural augmentation.

BACKGROUND OF THE INVENTION

Replacing or supplementing fractured, damaged, or degenerated mammalian skeletal bone with prosthetic implants made of biocompatible materials is commonplace in the medical arts. Most often, implant devices are intended to become permanently integrated into the skeletal structure. Unfortunately, permanent prosthetic attachment to bone is rare. Factors that influence long-term implant viability include material type used, bone fixation method, implant location, surgical skill, patient age, weight and medical condition. A plethora of devices have been constructed attempting to optimize these variables involved in producing an increase in bone fusion.

Common materials used in prosthetic devices include ceramics, polymers and metals. Currently, metallic materials afford the best mechanical properties and biocompatibility necessary for use as skeletal prosthetic implants. Frequently used metals include, titanium and titanium alloy, stainless steel, gold, cobalt-chromium alloys, tungsten, tantalum, as well as, similar alloys. Titanium is popular in the implant field because of its superior corrosion resistance, biocompatibility, physical and mechanical properties compared to other metals. The dramatic increase over the last decade of titanium material presentations in neurosurgical, orthopedic and dental surgery attests to its acceptance as a prosthetic material. Titanium presentations vary mostly in shape and surface type, which influence the implant's ability to support load and attach to bone.

A significant drawback to titanium implants is the tendency to loosen over time. There are three typical prevailing methods for securing metal prosthetic devices in the human body: press-fitting the device in bone, cementing them to an adjoining bone with a methacrylate-type adhesives, or affixing in place with screws. All methods require a high degree of surgical skill. For example, a press-fitted implant must be placed into surgically prepared bone so that optimal metal to bone surface area is achieved. Patient bone geometry significantly influences the success of press-fitted implants and can limit their usefulness as well as longevity. Similar problems occur with cemented implants; furthermore, the cement itself is prone to stress fractures and is not bio-absorbable. Therefore, all methods are associated to varying degrees with cell lysis next to the implant surface with concomitant fibrotic tissue formation, prosthetic loosening, and ultimate failure of the device.

Currently, methods are being developed that produce osteointegration of bone to metal obviating the need for bone cements. Osteointegration is defined as bone growth directly adjacent to an implant without an intermediate fibrotic tissue layer. This type of biologic fixation avoids many complications associated with adhesives and theoretically would result in the strongest possible implant-to-bone bond. One common method is to roughen a metal surface creating a micro or macro-porous structure through which bone may attach or grow. Several implant device designs have been created attempting to produce a textured metal surface that will allow direct bone attachment. Some of these devices are found in the following U.S. Pat. Nos. 3,894,297; 3,905,777; 3,906,550; 4,064,567; 4,199,824; 4,261,063; 4,430,761; 4,479,271; 4,530,116; 4,535,487; 4,536,894; 4,549,319; 4,570,271; 4,589,883; 4,608,053; 4,636,219; 5,018,285; 5,344,654; 5,373,621; 5,609,635; and 5,658,333.

Metallic implant surfaces are also commonly coated with micro-porous ceramics such as hydroxyapatite (HA) or beta-tricalcium phosphate (TCP) (see U.S. Pat. Nos. 4,309, 488; 4,145,764; 4,483,678; 4,960,646; 4,846,837). The former treatment is more common because calcium-phosphate salts tend to be absorbed, in vitro, and thus loose their effectiveness. The HA coatings increase the mean interface strength of titanium implants as compared to uncoated implants (see Cook et al., Clin. Ortho. Rel. Res., 232, p. 225, 1988). In addition, clinical trials in patients with hip prosthesis have demonstrated rapid bone growth on prosthetic devices and increased osteointegration of titanium alloy implants when coated with HA (see Sakkers et. al., J. Biomed. Mater. Res., 26, p. 265, 1997). The HA ceramic coatings can be applied with a plasma spray machine or by sintering (see U.S. Pat. No. 4,960,646). In addition, the HA coating can be applied by soaking the implant in an alkali solution that contains calcium and phosphorous and then heated to deposit a film of hyroxylapetite (see U.S. Pat. 5,609,633). Optimal HA coating thickness ranges from 50–100 microns (see Thomas, Orthopedics, 17, p. 267–278, 1994). If coated too thick the interface between the HA and bone becomes brittle. Despite the higher success rate of prosthetic devices coated with HA as compared to earlier implantation methods, failure over time still occurs. Again, proper integration requires that the surgeon create an exact implant fit into bone allowing the metal and bone surfaces to have maximum contact. Also, fibrotic tissue formation develops in some cases regardless of coating type.

Recent research describes the use of osteoinductive proteins to produce prosthetic osteointegration as well as increase the rate of bone formation next to implant surface (for example see Cole et. al., Clin. Ortho. Rel. Res., 345, p.21–228, 1997). Osteoinductive proteins are secreted signaling molecules that stimulate new bone production. These proteins include, PDGF, IGF-I, IGF-II, FGF, TGF-β and associated family members. The ability of these proteins to enhance osteointegration of metallic implants suggests that implants coated with these proteins may attach to bone more efficiently.

The most effective bone formation-inducing factors are the bone morphogenetic proteins (BMPs). The BMPs, a TGFβ super-family subset, share, along with the other members of its subgroup, strong sequence homology and conserved carboxyl-terminus cysteine residues. Over 15 different BMPs have been identified. Most members of this TGF-β subfamily stimulate the cascade of events that lead to new bone formation (see U.S. Pat. Nos. 5,013,649; 5,635,373; 5,652,118; and 5,714,589, reviewed in J. Bone Min. Res., 1993, v8, suppl-2, p.s565–s572). These processes include stimulating mesenchymal cell migration, osteoconductive matrix disposition, osteoprogenitor cell proliferation and differentiation into bone producing cells. Effort, therefore, has focused on BMP proteins because of their central role in bone growth and their known ability to produce bone growth next to titanium implants (see Cole et. al., Clin. Ortho. Rel. Res., 345, p.219–228, 1997). One such method claims achievement of a strong bond between existing bone and the prosthesis by coating the prosthetic device with an osteogenic protein (see U.S. Pat. No. 5,344,654).

In addition to osteoinductive proteins, osteoconductive factors may aid in bone formation (see U.S. Pat. No. 5,707,962). One experienced in the art realizes that osteoconductive factors are those that create a favorable environment for new bone growth, most commonly by providing a scaffold for bone ingrowth. The clearest example of an osteoconductive factor is the extracellular matrix protein, collagen. Other factors that can be considered osteoconductive include nutrients, anti-microbial and anti-inflammatory agents, as well as blood-clotting factors. In addition to these factors, reducing bone absorption by inhibiting osteoclast activity with bisphosphonate may also aid in implant success (see U.S. Pat. No. 5,733,564).

Bone morphogenetic protein-molecule presentation to skeletal tissue is critical for producing desired bone formation next to an implant device. Many matrix systems have been developed to contain and then steadily release bioactive peptides as the matrix degrades. Organic polymers such as polylactides, polyglycolides, polyanhydrides, and polyorthoesters, which readily hydrolyze in the body into inert monomers, have been used as matrixes (see U.S. Pat. Nos. 4,563,489; 5,629,009; and 4,526,909). The efficiency of BMP-release from polymer matrixes depends on the matrixes resorbtion rate, density, and pore size. Monomer type and their relative ratios in the matrix influence these characteristics. Polylactic and polyglycolic acid copolymers, BMP sequestering agents, and osteoinductive factors provide the necessary qualities for a BMP delivery system (see U.S. Pat. No. 5,597,897). Alginate, poly(ethylene glycol), polyoxyethylene oxide, carboxyvinyl polymer, and poly(vinyl alcohol) are additional polymer examples that optimize BMP-bone-growth-induction by temporally sequestering the growth factors (see U.S. Pat. No. 5,597,897).

Non-synthetic matrix proteins like collagen, glycosaminoglycans, and hyaluronic acid, which are enzymatically digested in the body, have also been used to deliver BMPs to bone areas (see U.S. Pat. Nos. 4,394,320; 4,472,840; 5,366,509; 5,606,019; 5,645,591; and 5,683,459). In human bone, Collagen serves as the natural carrier for BMPs and as an osteoconductive scaffold for bone formation. Demineralized bone in which the main components are collagen and BMPs has been used successfully as a bone graft material (see U.S. Pat. No. 5,236,456). The natural, or synthetic, polymer matrix systems described herein are moldable and release BMPs in the required fashion; however, used alone these polymers serve only as a scaffold for new bone formation. For example, U.S. Pat. Nos. 5,683,459 and 5,366,509 describe an apparatus, useful for bone graft substitute, composed of BMPs injected into a porous polylactide and hyaluronic acid meshwork. Furthermore, an osteogenic device capable of inducing endochondral bone formation when implanted in the mammalian body has been disclosed (see U.S. Pat. No. 5,645,591); this device is composed of an osteogenic protein dispersed within a porous collagen and glycosaminoglycan matrix. These types of devices were designed as an alternative bone graft material to replace the more invasive autograft procedures currently used. These devices by themselves would not work well as joint prosthesis due to their brittle nature and constant joint movement preventing bone formation into the device.

Proper implant load distribution is yet another characteristic important for correct prosthetic function. This issue prompted the development of a variety of devices that attempt to distribute the weight bearing load of the prosthetic implant or produce a direct bone-implant bond. For example, U.S. Pat. No. 5,639,237 describes an endosseous dental implant having a dimpled surface texture for use in crania-facial bones reconstruction. The indented surface increases contact area for bone proliferation, thereby enhancing the dental implant mechanical fixation or anchoring strength as compared to ordinary dental implants having a similar geometry. A similar prosthetic device manufacturing method for securing implant into human bone is described in U.S. Pat. No. 5,360,446. A description of an altogether different technique for enhancing bone density adjacent to the implant is in U.S. Pat. No. 5,344,457. This reference teaches that loading stress can be effectively transferred from a dental implant to surrounding bone through a tapered body shaped implant. Yet another technique is described in U.S. Pat. No. 5,458,653. This reference describes a prosthetic device coated with a bioabsorbable polymer in specific implant regions to, theoretically, better distribute the load placed upon it. Many other endosseous dental implants with shapes attempting to distribute load including helical wires, tripods, screws and hollow baskets have also been used. The clinical success of all these implant types is dependent on placement site, implant fit and the extent of fibrous tissue formation around the implant preventing direct bone contact.

Further complications arise when placing a prosthetic implant in skeletal areas that cannot support large functional loads and sheer stresses. Crania-facial implants, which are commonly used in the reconstruction or replacement of single teeth, are particularly prone to failure from stress. These prosthetic failures are primarily due to the inability of cancellous bone to support implant load. Unlike smooth, densely packed cortical bone, cancellous bone is porous and has an asymmetric sponge-like structure. In addition, small bones of the hand, elbow and feet that do not have thick cortical walls are prone to implant failure. Implants in these areas often fail due to excessive movement and a lack of supporting bone structure. For example, a prosthetic joint replacement device, when used in small hand bones, will often become loose and erode the surrounding bone due to lack of cortical structure. Methods, therefore, have been devised to augment or support porous or less dense bone.

One method for augmenting or supporting porous or less dense bone is provided in U.S. Pat. Nos. 4,693,721 and 5,030,233, wherein a biocompatible porous titanium-wire-mesh material is described for use in bone repair or replacement. Presumably, the porous mesh, when implanted, would allow bone ingrowth and distribute stress load while reinforcing areas of low density bone. Furthermore, according to U.S. Pat. Nos. 3,906,550, 4,660,755, 4,829,152 and 4,923,513, a porous titanium matrix can be welded onto a solid titanium prosthetic implant. Presumably, these methods would produce a broader load distribution across the titanium mesh surface, increase prosthetic implant surface area and load distribution, as well as reinforce bone areas that lack density. However, the fibrillar mesh of these described devices are cemented into place. In addition, these devices require that bone grow in-between the titanium-mesh is unaided by stimulating proteins. This bone growth is speculative and may or may not occur depending on the strength of the implantation site, bone health in the area treated, and the distance that the bone has to grow. In Michelson, U.S. Pat. No. 5,609,635, a method is described for the design of a spinal fusion device comprised of wire mesh infused with osteoinductive molecules. This device is intended solely for use in spinal fusions and is not designed for use with other prosthetic implants intended for use in other body areas. It is also not designed to be attached to orthopedic implants.

Despite the plethora of prior art approaches to securing an implanted structure into mammalian bone, there is a need in the medical and dental arts for improving the strength and integrity of the bone that surrounds and attaches to a prosthetic implant device. Furthermore, there is a need in these arts for a device that both produces osteoinductive-protein-induced bone formation between metal fibers and increases structural bone integrity, as well as the bone to implant contact area. As will be seen, the present invention provides a method and a structure for increasing strength and distribution of load bearing areas of the bone surrounding a prosthesis. In addition, the present invention provides a novel way to augment both endo and exo bone formation for a variety of applications.

SUMMARY OF THE INVENTION

A method and apparatus for bone augmentation in a mammalian body is presented. A primary application of the present invention is to support a prosthetic implant device. In one embodiment, a method and apparatus is provided for enhancing the mechanical strength of the prosthesis by reinforcement of bone in the region surrounding the implant device.

The method and apparatus comprises the formation of a number of fibrillar wires on the prosthetic implant device. In one embodiment, the formation of the fibrillar wires comprises cutting or gouging the implant device so that fibrillar wires or prongs are formed by peeling them from the implant device. In an alternate embodiment, the formation of the fibrillar wires comprises forming a mesh of fibrillar wires, wherein the wire is arranged into a woolly structure. The wool is formed around the prosthetic implant device, and a number of the fibrillar wires are attached to the prosthetic implant device. A semi-porous coating is formed on and between the fibrillar wires and the prosthetic implant device.

The coating comprises one or more osteoinductive factors such as a TGF-β family member, most likely a bone morphogenetic protein and an associated carrier matrix. Included in the coating with the osteoinductive factors may be one or more molecules that function as nutrients, anti-microbial compounds, anti-inflammatory agents, blood-clotting factors, angiogenic factors, and scaffolding molecules that hold these factors in place while potentiating bone ingrowth. The polymer may be comprised of lactic acid, glycolic acid polymers, and copolymers of lactic acid and glycolic acid. Furthermore, the coating may be comprised of an osteoinductive-protein-sequestering agent comprising monomeric and polymeric units of hyaluronic acid, alginate, ethylene glycol, polyoxyethylene oxide, carboxyvinyl polymer, and vinyl alcohol. Finally, the polymer may be composed of naturally occurring matrixes comprising collagen, glycosaminoglycan, or fragments of these or other proteins. Over time, bone formation between fibrillar wires of the wool reinforces the bone surrounding the prosthetic device producing a osteointegrated implant with optimal load distribution.

These and other features, aspects, and advantages of the present invention will be apparent from the accompanying drawings and from the detailed description and appended claims that follow.

BRIEF DESCRIPTION OF THE DRAWINGS

The objects, features, and advantages of the present invention will be apparent to one skilled in the art from the following detailed description in which.

DETAILED DESCRIPTION

The present invention provides a technique for constructing a prosthetic implant device that is well suited for osteointegration and load distribution. To provide a thorough understanding of the present invention numerous specific details are set forth including material types, dimensions, and procedures. Practitioners having ordinary skill in the biomedical arts will understand that the invention may be practiced without many of these details. In other instances, well-known devices, methods, and biochemical processes have not been described in detail to avoid obscuring the invention.

As discussed herein, chemically inert, biocompatible, strong, stable, and resilient implanted materials formed into various structures have been used in mammals to augment skeletal function and supplement bone integrity. Implant devices are typically cemented, screwed or force-fit into bone using various well-known procedures. In addition, the prosthetic implant surface may be roughened or coated to improve bone attachment to its surface. Current materials in use that meet biologic and surgical requirements include stainless steel, titanium, titanium alloys, chromium-cobalt alloys and other similar metals. Of these materials, titanium has the best biocompatibility as well as the necessary physical properties to produce strong flexible wires. For these reasons, titanium is the preferred metal in typical modem implants.

Prosthetic implant failure primarily occurs due to the inability of surrounding bone to support an implant load. The existing bone resorbs away from the implant because of improper load distribution or inflammatory osteolysis. The present invention offers a solution to the foregoing problem by providing a number of fibrillar wires attached at numerous points to a prosthetic implant device. The fibrillar wires and the device are coated with HA and encased in a carrier polymer containing osteoinductive and osteoconductive factors. These adherent compounds stimulate bone growth through the fibrillar wires, or through a titanium-wool mesh, producing complete implant osteointegration. Furthermore, the fibrillar wires enhance the structural integrity of the surrounding bone while the numerous device attachment points allow for optimal load distribution over then implant surface and existing bone.

Figure 1:
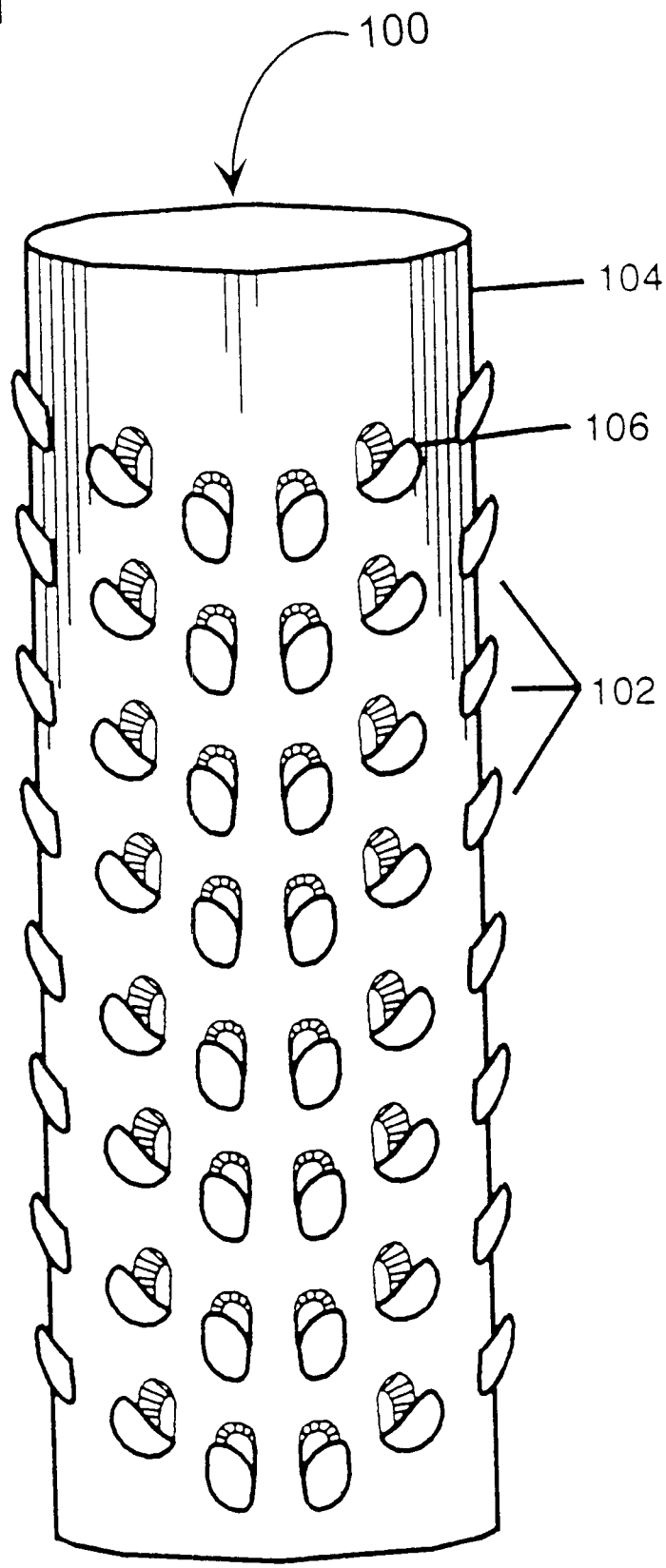
FIG. 1 is a center portion of a prosthetic implant device comprising fibrillar wires peeled from an implant core in accordance with an embodiment of the present invention.

FIG. 1 is a prosthetic implant device 100 comprising resulting groove 106 and fibrillar wires or prongs 102 peeled or gouged from the implant core 104 in accordance with an embodiment of the present invention. The fibrillar wires 102 are formed on the implant device 100 by physically gouging or cutting the implant core 104. Wire or prong formation is achieved by peeling the wires or prongs 102 from the core of the etched implant device.

Figure 2:
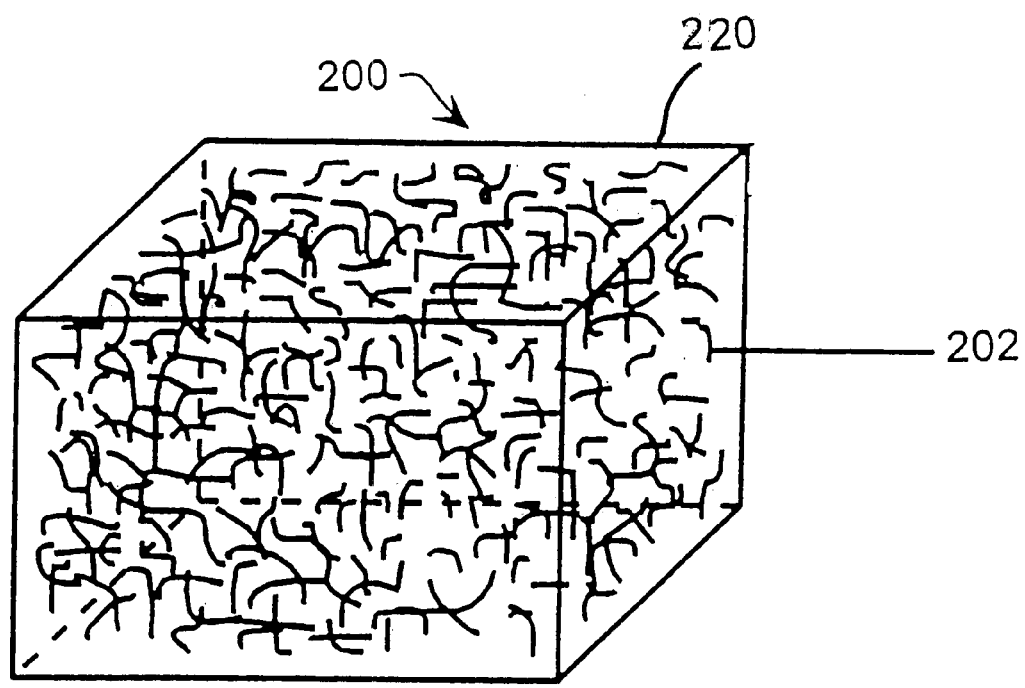
FIG. 2 is a fibrillar wire mesh formed into a woolly structure in accordance with an embodiment of the present invention.

FIG. 2 is a fibrillar wire formation 200 comprising a mesh of fibrillar wires 202 arranged into a wooly structure in accordance with an embodiment of the present invention. The mesh may be formed around a prosthetic implant device with a number of the fibrillar wires 202 of the mesh attached to the prosthetic implant device, but the embodiment is not so limited. A semi-rigid membrane 220 encapsulates the woolly structure. The membrane 220 can be made from a material such a collagen felt, polylatic acid, or polyether.

The fibrillar wool acts to provide sufficient surface area for bone attachment and to strengthen the surrounding bone matrix. In embodiments of the present invention, the fibrillar wire comprises titanium, titanium alloy, gold, stainless steel, or other inert, implantable metal alloys that may be manufactured in a thread-like form. In one embodiment, ordinary titanium wire is utilized having a diameter of approximately 10 to 1000 microns and a length of approximately 1 to 1000 mm, but the embodiment is not so limited. Furthermore, the wire shape may have a cross-section that is elliptical, rectilinear, or round. However, the embodiment is not so limited as the precise wire shape is not considered essential to the present invention.

Figure 3:
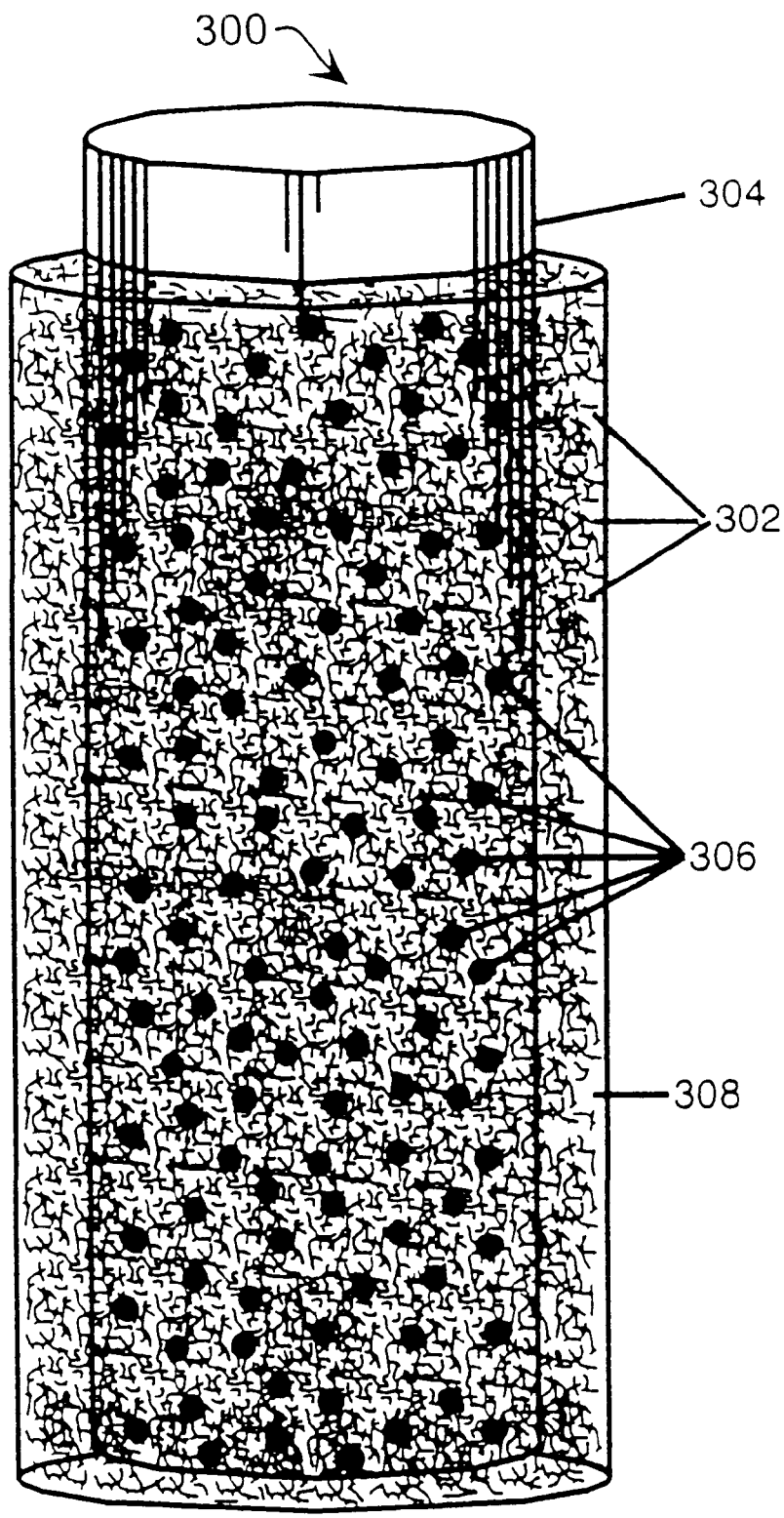
FIG. 3 is a prosthetic implant device comprising a fibrillar wire mesh attached to the prosthetic implant device core in accordance with an embodiment of the present invention.

FIG. 3 is a prosthetic implant device 300 comprising a fibrillar wire mesh 302 attached to a prosthetic implant device core 304 at particular points 306 in accordance with an embodiment of the present invention. The fibrillar wire mesh 302 may be attached to the implant device core 304 by the use of a material comprising solder, brazing material, and adhesive cement, but the embodiment is not so limited. Furthermore, the wool may be attached to the core prosthesis by direct metallurgic bonds, wherein typical procedures are used for producing metallurgic bonds comprising sintering and electric bonding.

Conventional manufacturing methods for commercial-grade steel wool are considered acceptable for producing the mesh of the present invention. One skilled in the art will realize wool construction can be achieved by many methods and combinations of various methods. The wool of an embodiment may be formed into a reproducible shape and porosity by placing it under mechanical pressure using a typical die cast tooling apparatus, but the embodiment is not so limited. Typical sintering operations comprise producing fiber metal-to-prosthetic core metal bonds by heating the metal and the prosthetic device core together under mechanical pressure in a vacuum furnace at a temperature range from 900 to 1300° Celsius (C) for 30 minutes to 4 hours; moreover, typical hydrogen-alloying treatments may be used in conjunction with the welding procedure.

Another typical method used in an embodiment of the present invention for producing metal bonds comprises forming spots by melting contact areas between a titanium wire and a prosthetic core with electrical currents. In this method, the mesh is formed into desired dimensions via mechanical pressure provided by the electrodes. Moreover, another typical method comprises using resistance welding of a porous metal body to a metal core substrate without concomitant changes in mesh geometry. This is achieved by pre-coating the porous body and core on all surfaces, except contact areas, with an electrically conductive material. The contact areas are etched to remove added conductive materials. Bonds are formed by application of 14,000 psi of mechanical pressure along with a current density equal to or greater than 15,000 amperes per square inch for a duration of at least five cycles. Under these conditions metal bonds form between the surface of the wool and the core prosthesis while maintaining mesh geometry.

Proper wool geometry and stimulation of bone in-growth into the wool matrix are central to an embodiment of the present invention. Bone in-growth involves osteoprogenitor cell migration, local activation of bone producing cells, angiogenesis, collagen matrix formation and mineral deposition. For the prosthesis to be effective, the wool must be both strong and porous to allow bone-formation in the spaces between the metal fibers. One skilled in the art will realize that the terms porosity or porous refer to varying densities of the wool. The wire mesh density should not be so low, or porous, as to provide an inadequate support matrix for enhancing bone strength in areas intended to support the prosthetic implant device. The estimated, optimal volume porosity is between 60 and 95% or a pore size of greater than 70 microns, but the embodiment is not so limited. Finally, the wool mesh may be made in such a manner as to allow molding of it by the surgeon to produce an outer prosthetic geometry to allow for maximum bone contact. Molding could be done by instruments available to the surgeon in the operating room.

Mesh porosity can be achieved by controlling the length, diameter and density of metal fibers, but the embodiment is not so limited. Typically, a pore size in the aforementioned range can be achieved using wire having a length of approximately 2 to 50 mm long and a diameter of approximately 20 to 200 microns, wherein a sintering operation strengthens the mesh. Typically, a biologically relevant mesh can be constructed by first bending the titanium wire in a sinusoidal design by passing it between a pair of spaced-apart meshed gears. The wire is then cut to various lengths and compressed in a cylinder producing a titanium wire mesh. Sintering increases the mesh strength. Furthermore, a typical method for creating a porous metal coating may use angled screen mesh layers bonded together. The arrangement of the fibrillar wires into the woolly structure may be random or may consist of a fabric having a more regular pattern, but the embodiment is not so limited.

An important aspect of the present invention is that new bone growth is induced to integrate with the structure formed by the system of fibrillar wires. The fibrillar wires function as reinforcing rods to provide multidirectional strength to the nascent bone and also distributes over a large internal surface area the physical forces placed upon the implant by body movement. The result is a more structurally secure prosthetic implant device that can withstand greater biomechanical forces. This integral characteristic of the wool mesh makes the present invention ideally suited for improving the strength and fixation of prosthetic devices.

In order to promote integrated bone growth in an embodiment of the present invention, several coating layers are formed on the fibrillar-wool-wires or prongs and the prosthetic implant device. The first layer comprises an oxide coating. The second layer comprises an applied HA coating. The third layer is a moldable-polymer-carrier material that localizes osteoinductive and osteoconductive factors, but the embodiment is not so limited. The oxide and HA layers create a microporous surface that is favorable for bone attachment, and acts to minimize metal ion release from the implant. Metal ion release is associated with stimulating inflammatory reactions resulting in osteolysis and implant failure. As metal implant osteointegration will only occur in the absence of inflammatory reactions, the oxide and HA layers of the present invention promote osteointegration.

The purpose of the moldable polymer coating 308 containing osteoinductive and osteoconductive proteins is to encourage bone growth into the wool-prosthesis by sequestering the bone-formation-stimulatory-proteins. Localized osteoinductive factors stimulate every aspect of bone formation including migration, proliferation and differentiation of bone producing cells thus promoting integration of graft and existing bone. In addition, the carrier polymer also serves as a barrier for infiltration of unwanted cell types.

Figure 4:
FIG. 4 is a portion of a filament or fibrillar wire of an embodiment of the present invention.

FIGS. 4–8 illustrate the steps of forming a coating on the fibrillar wires of an embodiment of the present invention. While the steps that accompany FIGS. 4–8 describe the process of forming a coating on the fibrillar wires, the same process may be used to form a coating on an associated prosthetic implant device. FIG. 4 shows a portion of a fibrillar wire 400 that comprises a metal such as titanium, titanium alloy, tantalum, gold, stainless steel, or other inert, implantable alloys that may be manufactured in a thread-like form, but the embodiment is not so limited.

Figure 5:
FIG. 5 is a transverse-section of a wire of an embodiment of the present invention having an oxide coating that covers an outer surface of the wire.

FIG. 5 is a transverse-section of a fibrillar wire 400 having an oxide coating 402 that covers the outer wire surface. In the case where the wire 400 comprises titanium, the oxide layer 402 comprises a titanium oxide that is formed naturally by contact with air and body fluids, but the embodiment is not so limited. Optimal oxide coating thickness is approximately 3–5 nanometers, but the embodiment is not so limited. Furthermore, implant devices can be subjected to a typical passivation treatment such as the ASTM-F86 protocol for nitric acid surface treatment, but the embodiment is not so limited.

Figure 6:
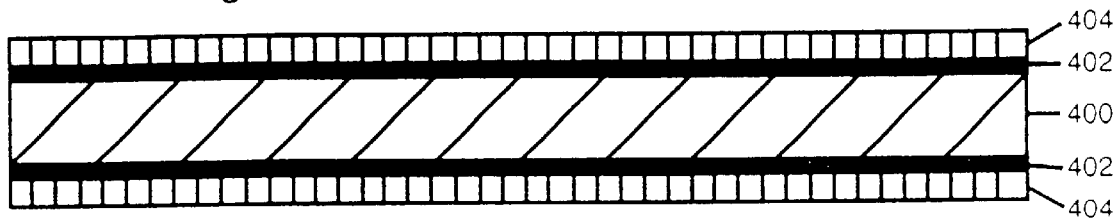
FIG. 6 is a transverse-section of a wire of an embodiment of the present invention having a hydroxyapatite layer coating an oxide layer.

Following oxide layer formation, or simultaneous therewith, the wire 400 may be sterilized using methods comprising plasma oxidation, Argon plasma-cleaning, ethylene oxide, ultraviolet light and autoclaving, but the embodiment is not so limited. Following oxidation and sterilization the wire 400 is coated with a synthetic bone material. In one embodiment, the synthetic bone material comprises hydroxyapatite, but the embodiment is not so limited. FIG. 6 is a transverse-section of the wire 400 having a hydroxyapatite layer 404 coating the oxide layer 402. The application of the hydroxyapatite may be performed according to typical methods, wherein the typical methods comprise using a vacuum plasma spray. However, because the wire 400 will be subjected to subsequent bending and twisting forces, the hydroxyapatite 404 should be diffusely applied. Diffuse coating of the wire 400 with hydroxyapatite 404, therefore, allows the wire 400 to be randomly bent and matted into a mesh. Optimal coating thickness is approximately 50 microns, but the embodiment is not so limited. The HA coating may be applied to the fibrillar wires before or after wool formation.

Figure 7:
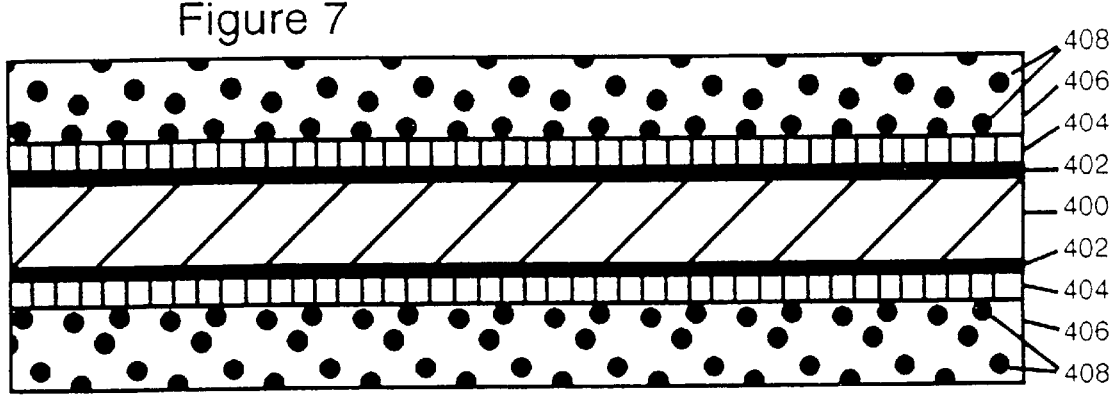
FIG. 7 is a transverse-section of a wire of an embodiment of the present invention having a carrier matrix containing osteoinductive and conductive factors coating an hydroxyapatite layer.

Following application of the hydroxyapatite, an osteoinductive protein-sequestering agent or carrier is applied. FIG. 7 is a cross-sectional portion of the wire 400 having a polymer 406 coating the hydroxyapatite layer 404. The polymer in the form of an osteoinductive-matrix coating 406 may be applied as a liquid or viscous gel substance that coats or is cultured onto the fibrillar wire 400. In addition, the osteoinductive-matrix coating may be molded onto the wire 400 or wool manually or with the use of die-casting molds. Incubating the wire 400 with osteoinductive proteins and polymer carrier together may alternatively form the osteoinductive-matrix coating 406.

The carrier provides for accelerated bone formation by serving as a reservoir for osteoinductive factors, wherein as the carrier dissolves it provides a sustained release system for these factors. Unsequestered purified osteoinductive proteins diffuse rapidly away from an implantation site and are typically unable to produce local bone growth. To work properly the carrier should not induce inflammation, should biodegrade in a timely fashion, and should allow body fluid and cell access. In addition, the carrier should be of such a consistency as to allow its molding and manual placement into and around the wool, but the embodiment is not so limited.

The carrier of one embodiment is a polymer comprising a porous matrix component selected from the group comprising polyanhydrides, monomers and polymers of D, L-lactic acid, D, L-glycolic acid, hyaluronic acid, alginate, ethylene glycol, oxyethylene oxide, carboxyvinyl, vinyl alcohol, and copolymers of mixtures of these compounds, but the embodiment is not so limited. Furthermore, the polymer may comprise a polylactic acid-polyethylene glycol copolymer and small particles of hydroxyapatite, salts such as sodium chloride as well as sugars like sucrose, but the embodiment is not so limited. Poly-D, L-lactic acid homopolymers with high molecular weights such as 21,000 d and greater are less favorable because they produce strong foreign-body reactions and are too slowly absorbed to produce bone growth.

The carrier matrix of an embodiment is not limited to synthetic polymers. For example, the use of natural carriers for osteoinductive factors such as collagen is acceptable. Collagen is a large extracellular matrix protein found in high concentrations (50–70% by weight) in bone. Purified reconstituted collagen binds readily to osteoinductive factors such as BMPs. In addition, fabrication of reconstituted collagen into a sponge-like structure with pores is possible. Collagen in this state can act as a scaffold for ingrowth of bone-producing cells. The collagen source may be both xenogeneic or allogeneic with respect to mammalian recipient. Typical known procedures can be used to isolate and purify collagen from collagen producing cell cultures, bone, tendon, and skin. Alternatively, recombinant collagen can be produced using typical molecular biologic techniques. For example, DNA coding sequences for collagen type IV, I and VI or truncated sequences can be placed in mammalian, insect or yeast expression vectors directly down-stream from strong viral promoters. These vectors can then be transfected into appropriate host cell culture systems resulting in collagen production in large quantities.

FIG. 7 further illustrates the location of osteoinductive factors 408 that have been formed into the osteinductive-matrix coating 406. A polymer-osteoinductive protein matrix can be formed by dissolving an acceptable polymer in a solvent such as ethanol and mixing in a solution of purified osteoinductive proteins, but the embodiment is not so limited. Moldable material may typically be achieved by precipitation with a second solvent. Alternatively, the mixture may be lyophilized to remove solvent creating a solid composite.

In the case of collagen-osteoinductive protein matrix, purified collagen can be solubilized and mixed with a purified solution of osteoinductive proteins using standard biochemical techniques. The concentration of purified osteoinductive factors should be sufficient to induce bone formation in vivo, wherein a typical concentration is approximately 5 to 400 micrograms of purified growth factors in 125 mg of matrix. Thus, an appropriate ratio of carrier to growth factor is approximately 100 to 1, but the embodiment is not so limited.

In one embodiment, the osteoinductive-matrix coating 406 comprises a substance that is applied to the fibrillar wires 400 prior to formation of the mesh. In an alternate embodiment, the woolly mesh may be formed first from the fibrillar wires, wherein the osteoinductive matrix is then infused into and around the wool matrix or peeled fibrillar wires. The carrier osteoinductive-matrix coating 406 stimulates new bone formation and increase the prosthetic implant osteointegration by stimulating every aspect of new bone formation and regeneration.

Osteoinductive factors of an embodiment comprise, but are not limited to, BMP-2 through 7, IGF-I, IGF-II, TGF-$\beta_1$, TGF-$\beta_2$, basic-FGF, acidic-FGF and PDGF or similar growth factors. Moreover, BMP hetero-dimers may be used such as BMP-2 combined with BMP-7 or BMP-6, and BMP-4 linked with BMP-7, but the embodiment is not so limited. BMPs may be isolated from bone using guanidinium chloride extraction or BMP-producing tumor cell-lines and purified to homogeneity using typical chromatographic techniques, but the embodiment is not so limited. Alternatively, expression of BMP-protein or bioactive fragments of BMPs using well-known recombinant-DNA expression and tissue culture systems, similar to those described for collagen, may be used to produce these proteins.

Osteoconductive factors used in the polymer-carrier-BMP coating of an embodiment comprise fibrinogen, $\alpha$-thrombin, anti-inflammatory agents, osteoclast inhibitors such as bisphosphonate, and matrix proteins such as fibronectin, and laminin, but the embodiment is not so limited. Bacterial infection is a well-known complication of bone surgeries. Therefore, the inclusion of antibiotics in the carrier matrix may aid in preventing infections.

In addition, because angiogenesis is critical to new bone formation, angiogenic factors such as tumor necrosis factor-$\alpha$, platelet derived endothelial cell growth factor, angiotropin, angiogenin, vascular endothelial growth factor and other proteins that stimulate blood vessel formation may be incorporated into the matrix.

Figure 8:
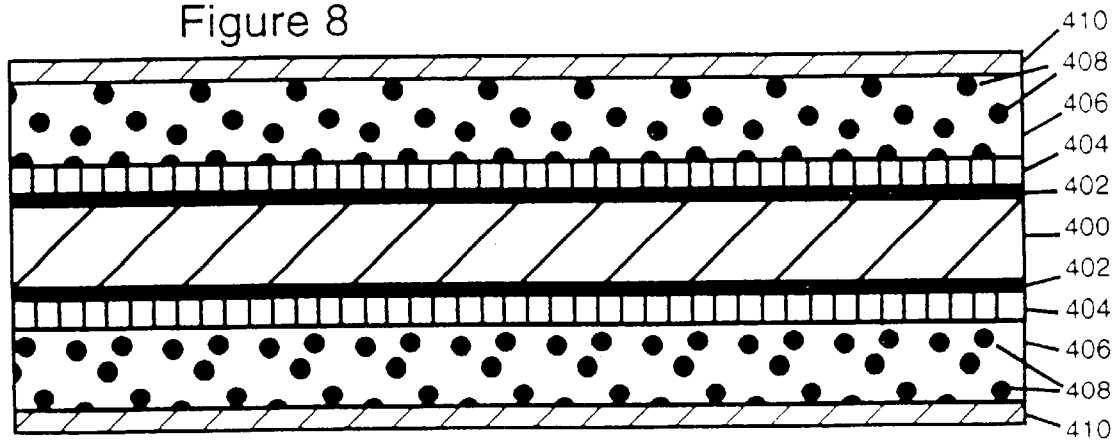
FIG. 8 is a transverse-section of a wire of an embodiment of the present invention having an outer coating comprised of an bio-absorbable, semi-porous polymer material covering the osteoinductive matrix layer.

Following addition of the osteoinductive-matrix coating 406 a final layer of a semi-porous polymer-matrix is applied. FIG. 8 is a transverse-section of the wire 400 having a semi-porous, bio-absorbable, polymer membrane layer 410. The purpose of this outer layer 410 is to encase the osteoinductive-matrix coating 406 aiding in the handling ease of the prosthetic device. It will also act as a barrier membrane to prevent infiltration of non-osteogenic cells. This process is known as guided tissue regeneration. This type of covering must be biodegradable or bio-absorbable. It must have a porous structure to allow passage of nutrients and fluids necessary for bone growth and cell viability. It should be moldable by common surgical instruments. It should have sufficient strength or a modulus of elasticity that enables it to be attached to bone or soft tissue using conventional surgical techniques such as, adhesives, press fitting, pinning or suturing in place.

Commonly used materials include collagen, polylactides and polyglycolides, similar to carrier materials described previously. The outer layer may be very similar to the osteoinductive-matrix layer but with additional requirements. It may also contain osteoinductive proteins.

Figure 9:
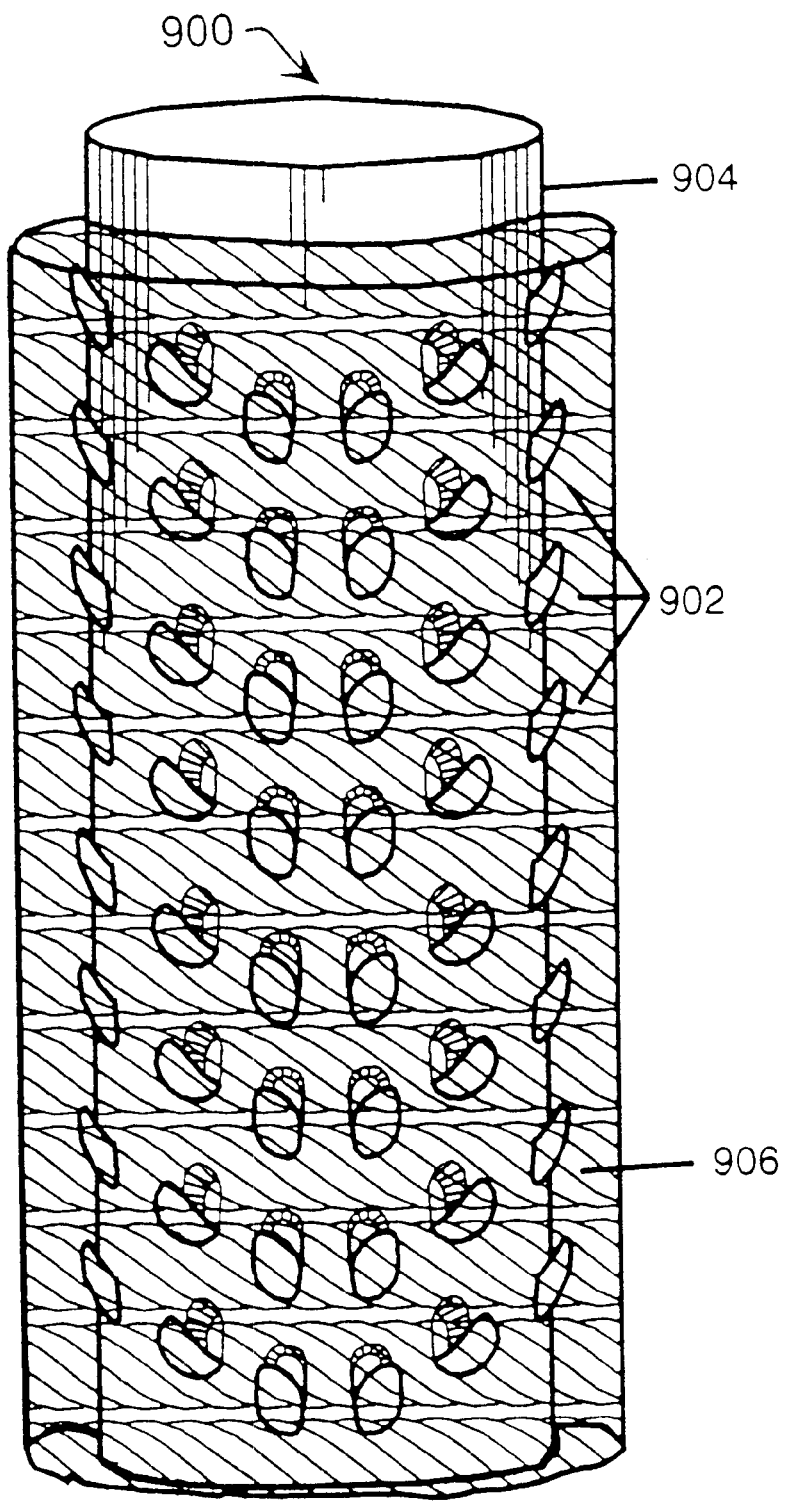
FIG. 9 is a prosthetic implant device comprising fibrillar wires or prongs peeled from an implant core and coated with moldable-carrier polymer containing osteoinductive and conductive factors.

FIG. 9 is a prosthetic implant device 900 comprising fibrillar wire 902 attached to a prosthetic implant device core 904 and an area comprising a polymer-carrier-osteogenic matrix 906 in accordance with an embodiment of the present invention. The prosthetic device 900, with a moldable, structurally reinforced outer coating or matrix 906 that stimulates bone formation, has several distinct advantages in orthopedic, dental, and neuro-surgery. A primary advantage of the moldable outer coating that stimulates osteointegration is a reduction in the surgical skill that is required to create maximum implant-to-bone surface contact. A moldable outer cover would allow the surgeon in the operating room to fit the implant into diversified bone contours, thus minimizing trauma to existing bone. Furthermore, over time, induction of bone growth into the fibrillar wire network fixes the prosthesis in place.

Another advantage of a reinforced-moldable osteoinductive coating is realized when the prosthetic device comprising the coating is used in areas of the body having weak bone structure. For example, hand and elbow prostheses are prone to failure because of low cortical mass surrounding the implant, which often will not support metal implant devices. Typically, metacarpophalangeal implants are made of silicone and are used as spacers in this joint; however, silicon spacers are poor at maintaining normal hand function. Metal implants that enable better joint function are prone to failure because metacarpal and phalangeal bones have thin cortical walls. The implant device 900 of an embodiment is used in these low density areas to reinforce the prosthesis site by stimulating bone growth, but the embodiment is not so limited.

A similar requirement for prosthesis site reinforcement occurs in mandibular bone. Normally the cortical bone layer that surrounds a tooth is capable of supporting the load of the associated tooth. Under conditions where tooth replacement is necessary, care must be taken to leave enough cortical bone surrounding a prosthesis to prevent its failure. If too much cortical bone is denuded the cancellous bone will not be able to support the large pressures placed on the tooth by occlusion. If an unstable graft site is created the cancellous bone must be supported. The implant device 900 of an embodiment of the present invention is used in the mandibular bone to stimulate bone growth.

Figure 10:
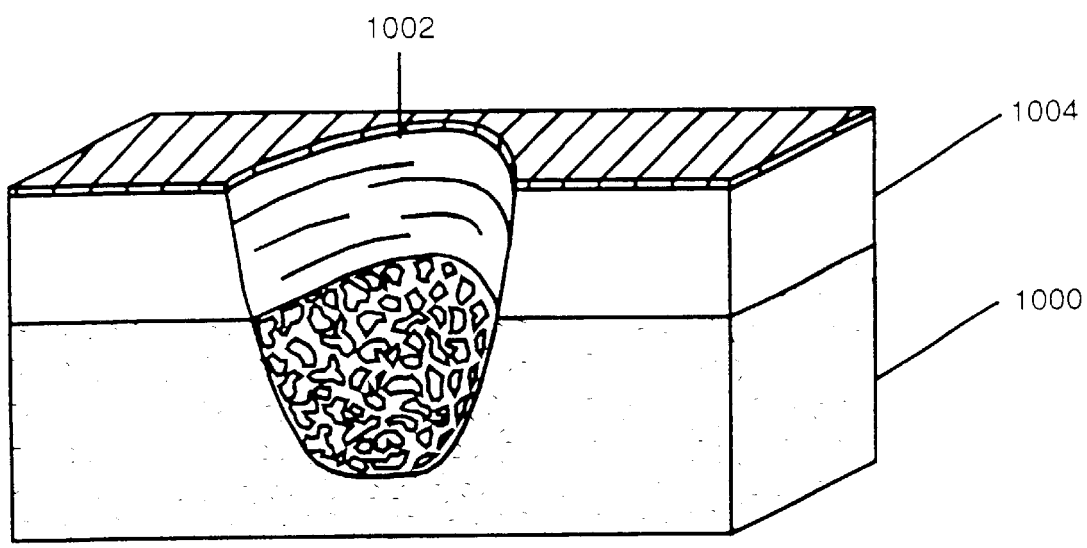
FIG. 10 is a transverse-section of bone having an opening or cavity surrounded by an epithelial tissue layer.

FIG. 10 is a transverse-section of bone 1000 having an opening or cavity 1002 surrounded by an epithelial tissue layer 1004. In the case of a dental implant, the cavity 1002 may represent the space created by avulsion of the natural tooth previously occupying that space. In other applications, the cavity 1002 may be created by the removal of either damaged or healthy bone in order to provide an receptor site for an implant device.

Figure 11:
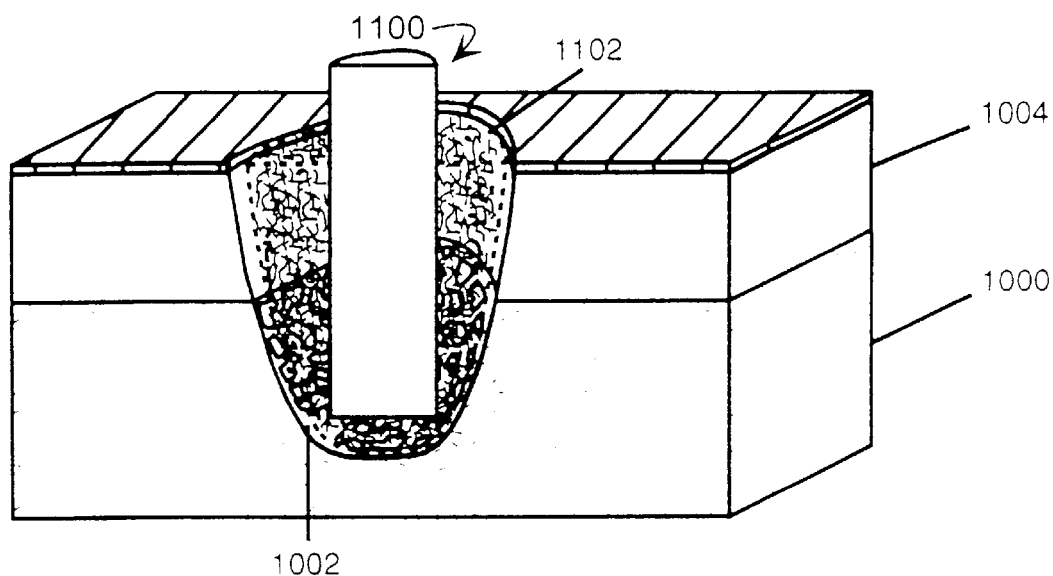
FIG. 11 is a transverse-section of bone cavity following insertion of a prosthetic implant device of an embodiment of the present invention.

FIG. 11 is a transverse-section of bone 1000 following insertion of a prosthetic implant device 1100 of an embodiment of the present invention into the cavity 1002. Prior to inserting the implant device 1100 into the cavity 1002, the cavity 1002 is cleaned and may be shaped utilizing conventional methods. Likewise, the fibrillar wires or mesh 1102 may be shaped to conform to the size of the bone cavity 1002. As discussed herein, the cavity 1002 may be created by the removal of a natural tooth. In other systemic instances, the cavity 1002 may result from a bone defect created, for example, by debridement of a dysplasia.

A barrier membrane (not shown) may be used to seal the fibrillar wires 1102 within the bone cavity 1002. Ideally, the barrier membrane seals the fibrillar wires within the bone cavity to prevent epithelial cell attachment 1004 to the fibrillar wires 1102. Without a suitable barrier membrane, mucosal attachment might extend into the fibrillar wires or mesh, thereby inhibiting bone growth. Prevention of mucosal attachment or soft tissue growth occurs by sealing off the fibrillar wires 1102 within the cavity 1002 with standard available products. Thus sealed, osteointegration of new bone growth into the mesh 1102 is permitted to occur. The membrane may comprise a bio-absorbable polymer the permits bone growth into the fibrillar wires. Non-absorbable material such as Gortex™ may also be used as a membrane. In some cases it may be desirable to reinforce the barrier membrane with titanium, or other medical grade materials. Ordinary thermoset resins or glues may also be utilized in the formation of the barrier membrane.

To secure the fibrillar wires 1102 within the bone cavity 1002, an adhesive material may be applied to the inner wall of the cavity, and/or to the outer surface of the fibrillar wires. Fibron glue is a suitable adhesive material for this purpose.

Bone growth into the fibrillar wires or mesh may be stimulated by energizing one or more of the fibrillar wires. For example, applying a relatively low-level electrical current such as 5–20 microamperes is sufficient to stimulate bone growth into the mesh-filled cavity, but the embodiment is not so limited. Of course, other forms of energy may also be used, such as radio frequency (RF) waves, microwaves, infrared radiation, or ultraviolet radiation, but the embodiment is not so limited. By way of example, a RF probe may be utilized to energize the entire fibrillar wire structure, thereby promoting adhesion of the mesh to the bone and stimulation of new bone growth.

The advantage of this invention is not limited to prostheses implanted directly into bone. For example, cage-like structures comprising cervical spinal fixation devices, carbon fiber cages, and metal sponges are commonly used as inserts into interbody spaces of the lumbar vertebrae after discectomies. The moldable wool-osteogenic device described in an embodiment of the present invention is ideally suited to stabilize vertebral bones and prevent postoperative collapse. In addition, this invention does not require additional surgeries necessary to extract autologous bone, which is used to provide a substrate for new bone growth. Osteogenic proteins incorporated into wool matrix would stimulate bone growth and preclude the need for bone grafts.

An important mechanism by which the present invention promotes bone growth into the fibrillar wires is through the use of a BMP coating. In this respect, it should be appreciated that culturing of the BMP onto the wire may be performed in vivo or in vitro. The BMP induces new bone growth resembling endochondral bone formation, which is integrated with the woolly structure of the fibrillar wires or mesh. The BMP also facilitates endogenous bone formation around the coated wire. The osteointegrated matrix comprising new bone attached to and reinforced by the fibrillar wires, provides improved mechanical strength and fixation for the prosthetic implant device. Over time, it is expected that the bone will further integrate onto the surface layer of implant device.

The invention has been described in conjunction with the preferred embodiment. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A mesh for bone augmentation comprising at least one fibrillar wire arranged in a woolly structure, the at least one fibrillar wire having an oxide layer, the mesh comprising a coating on and between the at least one fibrillar wire, wherein the coating comprises a carrier-polymer and osteoinductive and osteoconductive proteins, wherein osteointegration is promoted into the woolly structure when the mesh is placed in a mammalian bone.

2. The mesh of claim 1 wherein the at least one fibrillar wire comprises a metal selected from the group consisting of titanium, tungsten, gold, and stainless steel.

3. The mesh of claim 1 wherein the at least one fibrillar wire has a thickness in the range of 100 to 300 microns.

4. The mesh of claim 1 further comprising a semi-rigid membrane that encapsulates the woolly structure.

5. The mesh of claim 4 wherein the membrane comprises a material selected from the group consisting of collagen felt, polylatic acid, and polyether.

6. The mesh of claim 1 wherein the woolly structure includes a fibron glue coating for adhering the mesh to the mammalian bone.

7. The mesh of claim 1 wherein the oxide layer has a thickness in the range of 300–500 nanometers.

* * * * *